United States Patent
Massa et al.

(10) Patent No.: US 9,863,987 B2
(45) Date of Patent: Jan. 9, 2018

(54) APPARATUS AND METHODS FOR DYNAMIC PASSIVE INTERMODULATION DISTORTION TESTING

(71) Applicant: CommScope Italy S.r.l., Agrate Brianza (MB) (IT)

(72) Inventors: Riccardo Massa, Treviglio (IT); Vito Caggiano, Brugherio (IT); Gianluca Ratti, Carnate (IT)

(73) Assignee: CommScope Italy S.r.l. (IT)

( * ) Notice: Subject to any disclaimer, the term of this patent is extended or adjusted under 35 U.S.C. 154(b) by 0 days.

(21) Appl. No.: 15/335,733

(22) Filed: Oct. 27, 2016

(65) Prior Publication Data

US 2017/0122990 A1    May 4, 2017

Related U.S. Application Data

(60) Provisional application No. 62/250,068, filed on Nov. 3, 2015.

(51) Int. Cl.
  *G01R 23/20* (2006.01)
  *G01N 3/34* (2006.01)
  *G01R 31/28* (2006.01)

(52) U.S. Cl.
  CPC .............. *G01R 23/20* (2013.01); *G01N 3/34* (2013.01); *G01R 31/2853* (2013.01)

(58) Field of Classification Search
  None
  See application file for complete search history.

(56) References Cited

U.S. PATENT DOCUMENTS

| 4,648,124 A * | 3/1987 | Mantovani | H04B 17/20 324/520 |
| 9,354,262 B2 * | 5/2016 | Yagi | G01R 23/20 |
| 2002/0094785 A1* | 7/2002 | Deats | H04B 1/1027 455/67.13 |
| 2009/0096466 A1* | 4/2009 | Delforce | H04B 17/345 324/612 |
| 2016/0187243 A1* | 6/2016 | Schwab | G01N 3/30 73/12.09 |
| 2017/0115334 A1* | 4/2017 | Symes | G01R 29/105 |

OTHER PUBLICATIONS

Rosenberger, "Passive Intermodulation Analyzers" Rack, Desktop and Site Types, www.rosenberger.com.
Hartman, Rick et al., "PIM Test Power Levels for Mobile Communications Systems," Kaulus, www.kaelus.com; accessed Oct. 19, 2015.
Ludvik, Steve, Advanced Passive Intermodulation (PIM) Test System, Agilent Technologies, Aug. 29, 2013.

* cited by examiner

Primary Examiner — Patrick Assouad
Assistant Examiner — Demetrius Pretlow
(74) Attorney, Agent, or Firm — Myers Bigel, P.A.

(57) ABSTRACT

A passive intermodulation ("PIM") distortion test apparatus includes a housing, hammering elements disposed within the housing, each hammering element including a moveable striking member, a strike plate positioned above the hammering elements, where a bottom surface of the strike plate is positioned at a distance above the hammering elements such that the moveable striking members of the hammering elements impact the strike plate when moved into their activated positions, and a retaining member that is configured to hold a device under test on a top surface of the strike plate while a PIM distortion test is performed on the device under test.

20 Claims, 9 Drawing Sheets

US 9,863,987 B2

APPARATUS AND METHODS FOR DYNAMIC PASSIVE INTERMODULATION DISTORTION TESTING

CROSS-REFERENCE TO RELATED APPLICATION

The present application claims priority under 35 U.S.C. §119 to U.S. Provisional Patent Application Ser. No. 62/250,068, filed Nov. 3, 2015, the entire content of which is incorporated herein by reference as if set forth in its entirety.

FIELD OF THE INVENTION

The present invention relates generally to communications systems and, more particularly, to equipment and methods for testing components used in radio frequency ("RF") communications systems.

BACKGROUND

Passive Intermodulation ("PIM") distortion is a form of electrical interference that may occur when two or more RF signals encounter non-linear electrical junctions or materials along an RF transmission path. Such non-linearities may act like a mixer causing new RF signals to be generated at mathematical combinations of the original RF signals. If the newly generated RF signals fall within the bandwidth of existing RF signals, the noise level experienced by those existing RF signals is effectively increased. When the noise level is increased, it may be necessary reduce the data rate and/or the quality of service. PIM distortion can be an important interconnection quality characteristic for an RF communications system, as PIM distortion generated by a single low quality interconnection may degrade the electrical performance of the entire RF communications system. Thus, ensuring that components used in RF communications systems will generate acceptably low levels of PIM distortion may be desirable.

PIM distortion may be caused by, for example, inconsistent metal-to-metal contacts along an RF transmission path, particularly when such inconsistent contacts are in high current density regions of the transmission path such as inside RF transmission lines, inside RF components, or on current carrying surfaces of an antenna. Such inconsistent metal-to-metal contacts may occur, for example, because of contaminated and/or oxidized signal carrying surfaces, loose connections, metal flakes or shavings inside RF connections and/or poorly prepared RF terminations (e.g., a poor termination of a coaxial cable into a coaxial connector). PIM distortion may arise in a variety of different components of an RF communications system. For example, non-linearities may exist at the interconnections in an RF communications system where cables such as coaxial cables are connected to each other or to RF equipment. PIM distortion may also arise in other components of an RF communications system such as RF amplifiers, duplexers, cross-band couplers, interference mitigation filters and the like. PIM distortion may also arise on or within radiating elements of the RF communications system such as parabolic antennas or phased array antenna elements. The non-linearities that give rise to PIM distortion may be introduced at the time of manufacture, during installation, or due to electro-mechanical shift over time due to, for example, mechanical stress, vibration, thermal cycling, and/or material degradation.

PIM testing is routinely performed to identify components and/or interconnections that exhibit unacceptably high levels of PIM. International standard IEC 62037 sets out acceptable techniques for measuring PIM. Typically, various components of an RF transmission system will be rated to have PIM levels below certain ranges when tested according to the above-referenced international standard. PIM measurements may specify, for example, a magnitude of a third order intermodulation distortion signal. The PIM measurement may also specify operating characteristics of the device under test during the PIM distortion test. For example, for a tower mounted amplifier, the PIM measurement may specify the gain setting of the amplifier during the PIM distortion test.

SUMMARY

Pursuant to embodiments of the present invention, a PIM distortion test apparatus is provided that includes a housing with hammering elements therewithin, each hammering element including a moveable striking member, a strike plate positioned above the hammering elements, where a bottom surface of the strike plate is positioned at a distance above the hammering elements such that the moveable striking members of the hammering elements impact the strike plate when moved into their activated positions, and a retaining member that is configured to hold a device under test on a top surface of the strike plate while a PIM distortion test is performed on the device under test.

Pursuant to further embodiments of the present invention, methods of performing a PIM distortion test are provided in which a device under test is placed on an upper surface of a strike plate of a test station that includes a plurality of hammering elements located underneath the strike plate; a retaining member is positioned to engage at least one of a top surface or a side surface of the device under test to pin the device under test against the strike plate; the hammering elements of the test station are activated according to a pre-programmed sequence, where activation of each hammering element causes a moveable striking member of the hammering element to extend upwardly to impact a lower surface of the strike plate; at least two RF signals are transmitted through the device under test while the hammering elements are activated according to the pre-programmed sequence; and a spectrum analyzer is used to measure PIM distortion generated in the device under test while the hammering elements are activated.

DETAILED DESCRIPTION

Figure 1:
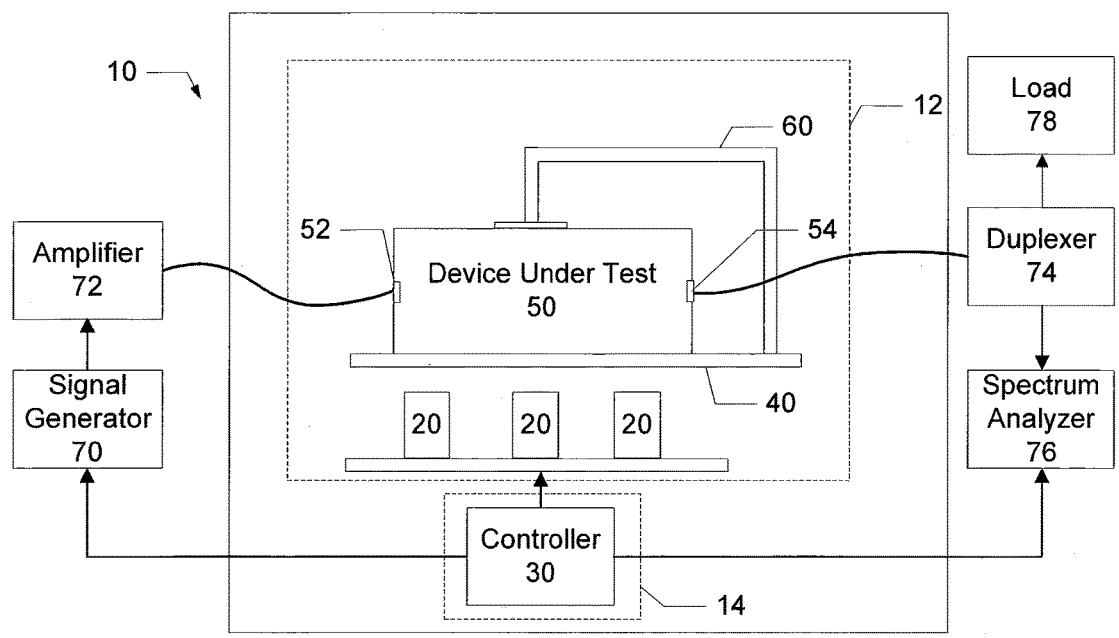
FIG. 1 is a block diagram of a PIM distortion test apparatus according to certain embodiments of the present invention.

Measuring and controlling the levels of PIM distortion may be important for providing high performance RF communications systems. Unfortunately, PIM distortion measurements are difficult to perform, and the measurements may be influenced by a variety of factors that may cause the measurements to inaccurately reflect the true PIM distortion levels. As discussed above, microscopic metal shavings or poor metal-to-metal connections are two common sources of PIM distortion. However, in a static environment, such potential PIM generators may not necessarily give rise to PIM distortion during a PIM distortion test. By way of example, metal shavings that are present within a device under test may not be positioned during the test at locations where they give rise to PIM distortion. Over time, these metal shavings may migrate in response to movement of the device under test, vibrations, or the like and some of the metal shavings may end up in locations where they give rise to significant PIM distortion.

In light of the above, to more accurately model the PIM performance of a device under test, the normal practice is to softly hammer or otherwise tap the device under test. In fact, the above-referenced international standard IEC 62037 expressly recommends that "devices should be subjected to impact or movement while PIM testing." This test practice is commonly referred to as "dynamic PIM distortion testing." The normal industry practice is to have a human operator manually tap the device under test with a rubber mallet during the PIM distortion testing. Vibration tables have also been used instead of manual hammering to produce mechanical stress during PIM distortion testing, but this technique appears to be less effective than manually striking the device under test with a rubber mallet.

One problem with conventional dynamic PIM distortion testing techniques is that manual hammering by a human operator cannot be accurately reproduced from test-to-test as it is not possible to accurately replicate numerous factors of the hammering test including the locations where the hammer strikes the device under test, the time between hammer strikes, the amount of force applied by each hammer strike, and the direction at which the force is applied.

Pursuant to embodiments of the present invention, test apparatus for PIM distortion testing and related methods of PIM distortion testing are provided which may significantly increase the repeatability of a dynamic PIM distortion measurement. These test apparatus may include one or more hammering elements that directly or indirectly apply a force to a device under test during a PIM distortion measurement test. In an example embodiment, the hammering elements may be pneumatic actuators. In some embodiments, the test apparatus may include at least one rigid strike plate that is placed above the pneumatic actuators. Each pneumatic actuator includes a piston that is received within a cylinder. The piston is forced upwardly to project from the cylinder when the pneumatic activator is activated or "fired." The strike plate is positioned above the pistons so that when the pneumatic actuators are fired, the pistons shoot upwardly and strike the lower surface of the strike plate. The device under test is positioned on the upper surface of the strike plate opposite the pneumatic actuators. Since the strike plate is formed of a rigid material such as a metal, the energy transferred by the piston of each pneumatic actuator to the lower surface of the strike plate passes through the strike plate to the device under test.

The test apparatus according to embodiments of the present invention may be programmable so that different "strike patterns" may be applied. Each strike pattern may specify, for example, which hammering elements strike the strike plate, when each such strike occurs and the number of strikes made by each hammering element. Thus, different strike patterns may be used for the same or different devices under test, and the dynamic PIM distortion tests performed using the test apparatus according to embodiments of the present invention may be fully repeatable simply by mounting the device under test in the same location on the strike plate and by using the same strike pattern when performing the dynamic PIM distortion test.

Example embodiments of the present invention will now be discussed in further detail with reference to the drawings.

FIG. 1 is a block diagram of a PIM distortion test apparatus 10 according to certain embodiments of the present invention.

As shown in FIG. 1, the PIM distortion test apparatus 10 includes a plurality of hammering elements 20 that are controlled under the operation of a controller 30. The hammering elements 20 are positioned adjacent a first side of a strike plate 40. The hammering elements 20 are positioned close enough to the strike plate 40 so that, when activated, a moveable striking member of each hammering element 20 will impact the first side of the strike plate 40 to impart a force to the strike plate 40. The controller 30 may control operation of the hammering elements 20 including, for example, which hammering elements 20 impact the strike plate 40, the sequence in which the different hammering elements 20 impact the strike plate 40, and the number of times each hammering element 20 impacts the strike plate 40.

A device under test 50 is positioned on a second side of the strike plate 40 that is opposite the first side. A retaining member 60 is provided that may be used to hold the device under test 50 firmly against the strike plate 40.

As is further shown in FIG. 1, the PIM distortion test apparatus 10 is used in conjunction with electronic equipment that generates the test signals that are provided to the device under test and measures the resulting PIM distortion levels. Such equipment is sometimes referred to as the "PIM bench." As shown in FIG. 1, in one example configuration this electronic equipment may include an RF signal generator 70, an amplifier 72, a duplexer 74, a spectrum analyzer 76, and a load 78. The RF signal generator 70 may be controlled by the controller 30. The signal generator 70 may generate the RF signals that are transmitted to the device under test during the PIM distortion test. The RF signals that are generated by the signal generator 70 may be output to the amplifier 72 which amplifies these signals to a level appropriate for a PIM distortion test. The amplified RF test signals are fed from the amplifier 72 to an input port 52 on the device under test 50 via, for example, a coaxial cable. The RF test signals pass through the device under test 50 and exit the device through an output port 54. The output port 54 may be connected by, for example, a coaxial cable to a duplexer 74 that separates the transmit band signals from the receive band signals, as it is the receive bandwidth that is susceptible to PIM distortion. The transmit band signals are routed by the duplexer 74 to the load 78, which dissipates the signal energy. The receive band signals are routed by the duplexer 74 to the spectrum analyzer 76. The spectrum analyzer 76 measures and records the levels of PIM present in the receive bandwidth. The spectrum analyzer 76 may also be under the control of the controller 30. Other elements may also be included in the test set-up. It will be appreciated that the PIM bench may take on many different forms, and is not limited to the configurations shown in FIG. 1 and/or otherwise discussed herein. For example, integrated PIM testers are available in which all of the equipment is integrated into a single device. It will also be appreciated that the PIM bench may partly or wholly be incorporated into the PIM distortion test apparatus 10. The controller 30 may have the capability to control some or all of the PIM bench in example embodiments.

In order to conduct a PIM distortion test, the controller 30 may cause the signal generator 70 to generate appropriate RF test signals that are fed to the device under test 50 through the amplifier 72. The spectrum analyzer 76 may measure and record the amount of PIM distortion that results from the RF test signals. During the initial part of the test, the hammering elements 20 may be inactive, and hence the initial part of the test may comprise a static PIM distortion test. Thereafter, the controller 30 may control the hammering elements 20 to perform a strike pattern to conduct a dynamic PIM test. The spectrum analyzer 76 may measure and record the amount of PIM distortion that results during both the static and dynamic portions of the PIM distortion test. A second static PIM distortion test may be performed after the dynamic PIM distortion test is completed. Of course, in other embodiments the test may be solely a dynamic PIM distortion test, or different sequences of static and dynamic PIM distortion tests.

In some embodiments, the PIM distortion test apparatus 10 may be implemented as a single unit. In other embodiments, the PIM distortion test apparatus 10 may include multiple separate items. For example, in some embodiments, a first unit in the form of a test station 12 may be provided that includes the hammering elements 20, the strike plate 40 and the retainer 60. The device under test 50 may be mounted on this first unit (i.e., on test station 12). The controller 30 may be a separate second unit in the form of a control station 14. The signal generator 70, the amplifier 72, the filter 74 and the spectrum analyzer may be implemented as one or more additional units or, for example, may be incorporated into the control station 14.

A PIM distortion test apparatus 100 according to embodiments of the present invention that includes a test station 102 and a control station 104 will now be described with reference to FIGS. 2-11. FIGS. 3-7 illustrate the test station 102 in further detail. FIGS. 8-11 illustrate the control station 104 in further detail.

Figure 2:
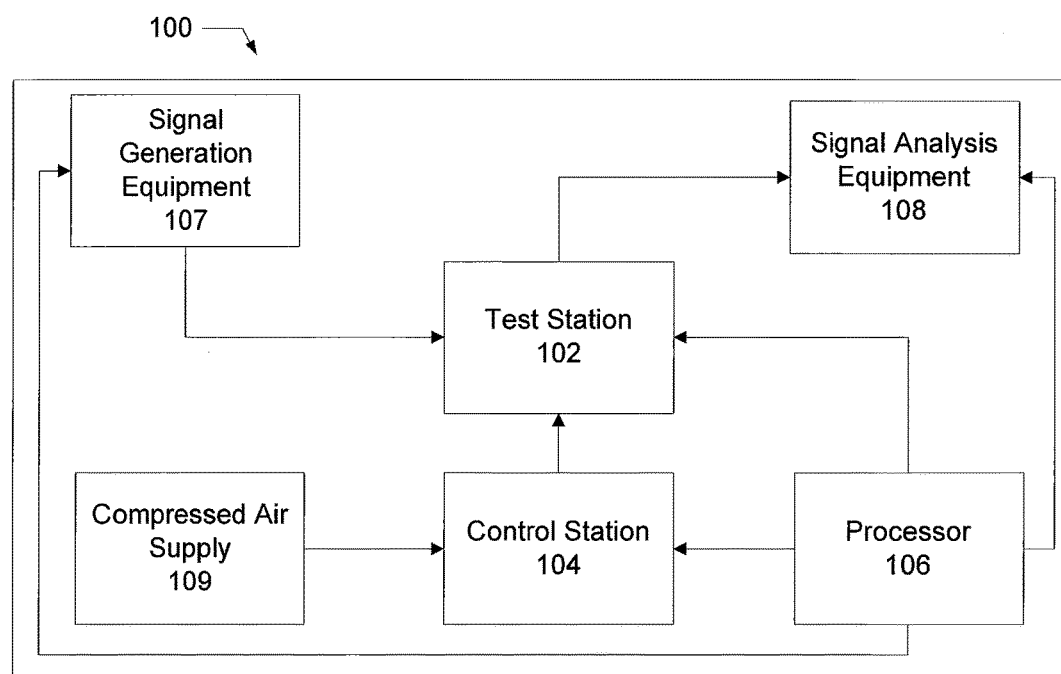
FIG. 2 is a block diagram of a PIM distortion test apparatus according to further embodiments of the present invention.

FIG. 2 is a block diagram of the PIM distortion test apparatus 100. The PIM distortion test apparatus 100 includes a test station 102, a control station 104, a processor 106, signal generation equipment 107, signal analysis equipment 108 and a compressed air supply 109. The processor 106 may comprise, for example, an external computer in some embodiments. The processor 106 may be in communication with one or more of the test station 102, the control station 104, the signal generation equipment 107 and/or the signal analysis equipment 108 via wired and/or wireless connections. In some embodiments, the processor 106 may be integrated into the test station 102 or the control station 104. The test station 102 and the control station 104 may also be implemented as a single unit in some embodiments. The signal generation equipment 107 and/or the signal analysis equipment 108 may each be one or more separate units or may also be integrated into, for example, the test station 102 or the control station 104.

The control station 104 is also operatively coupled to the test station 102. The compressed air supply 109 provides compressed air to the control station 104. Control station 104 may supply compressed air to hammering elements within the test station 102 under the control of the processor 106. The signal generation equipment 107 may be coupled to the test station 102 to provide RF signals to the test station 102 that are used in the PIM distortion test, and the signals output from the test station 102 during such tests may be provide to signal analysis equipment 108 that is used to measure PIM distortion levels.

Figure 3:
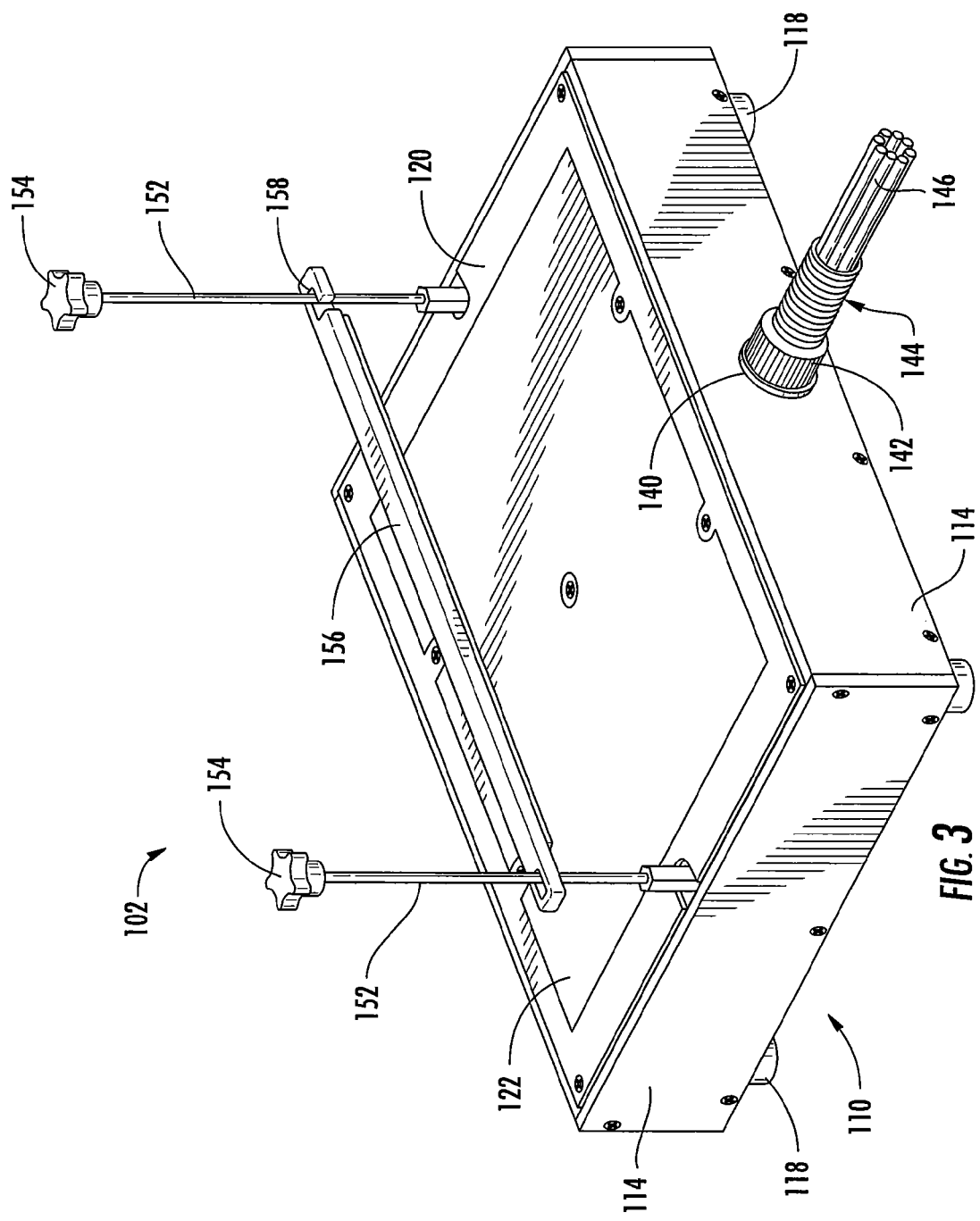
FIG. 3 is a perspective view of a test station of the PIM distortion test apparatus of FIG. 2.
Figure 4:
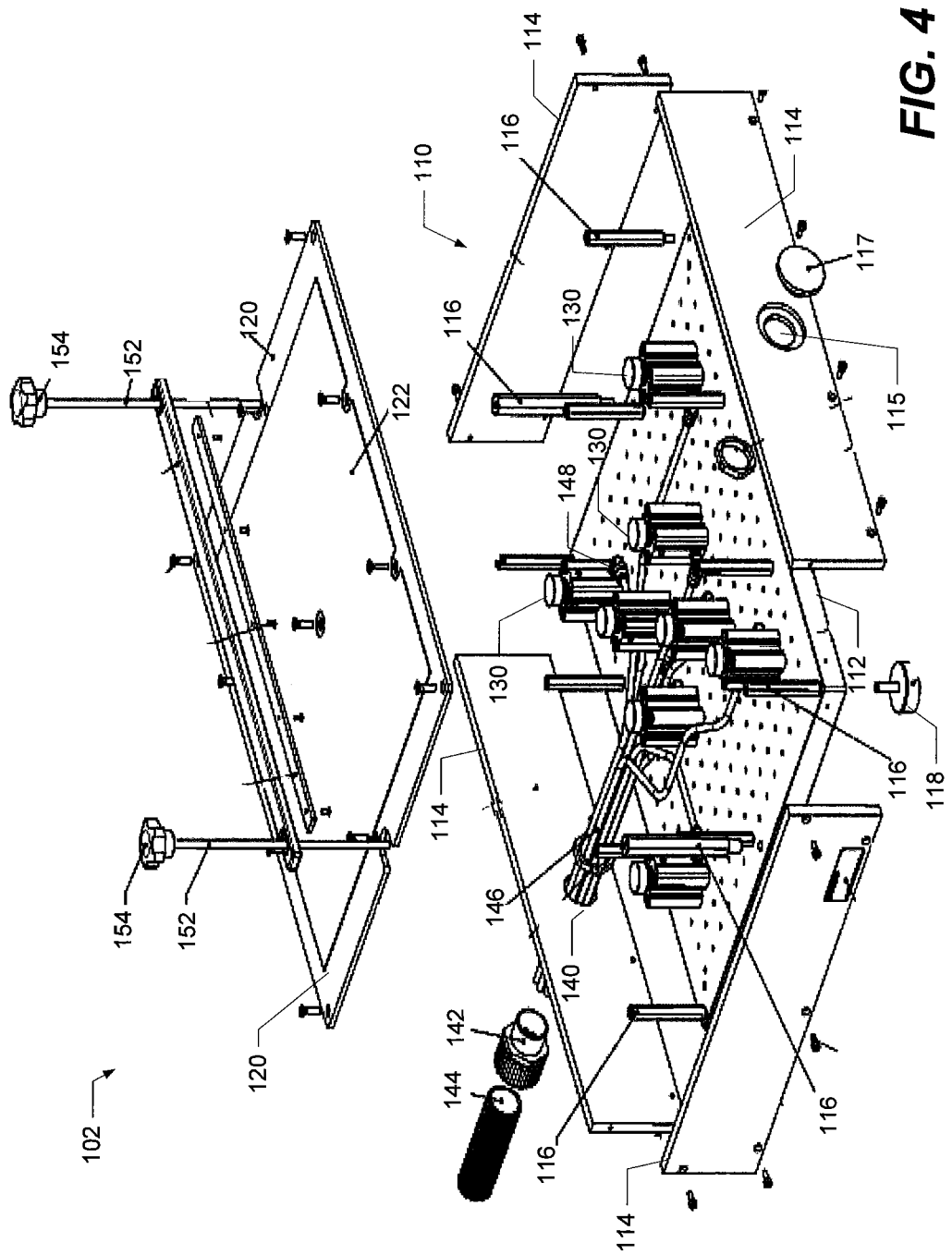
FIG. 4 is an exploded perspective view of the test station of FIG. 3.
Figure 5:
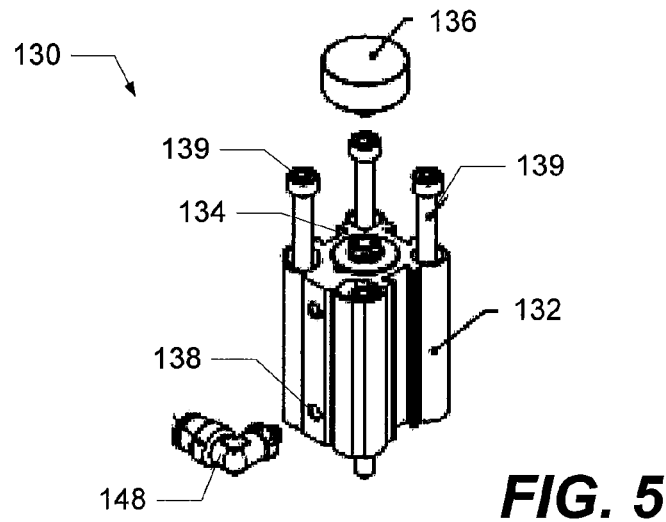
FIG. 5 is a perspective view of one of the pneumatic actuators included in the test station of FIGS. 3-4.
Figure 6:
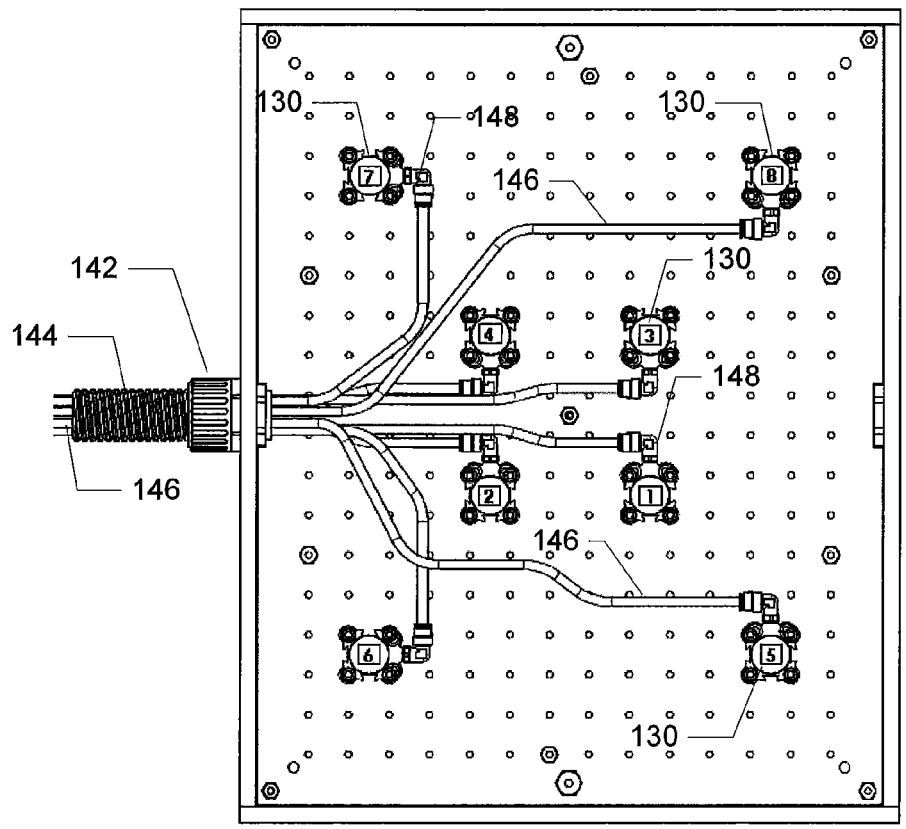
FIG. 6 is a top view of the test station of FIGS. 3-4 with the strike plate thereof removed to expose the interior thereof.
Figure 7:
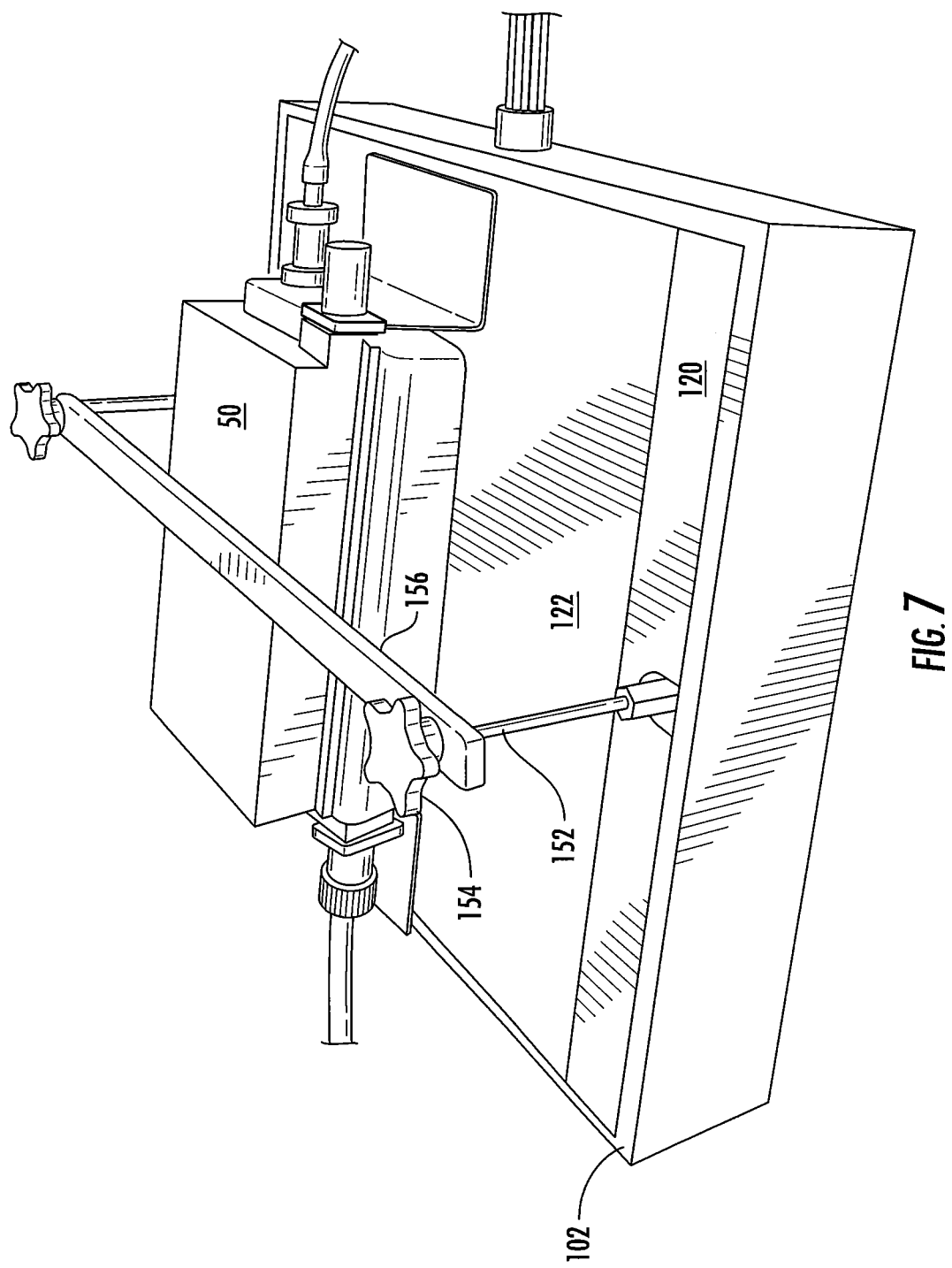
FIG. 7 is a perspective view of the test station of FIGS. 3-4 with a device under test mounted on the strike plate thereof.

Referring next to FIGS. 3-7, FIGS. 3 and 4 are a perspective view and an exploded perspective view, respectively, of the test station 102. FIG. 5 is a perspective view of one of the pneumatic actuators included in the test station 102. FIG. 6 is a top view of the test station 102 with the top plate of the housing thereof removed to expose the interior thereof. FIG. 7 is a perspective view of the test station 102 with a device under test mounted on the strike plate thereof.

Referring to FIGS. 3 and 4, the test station 102 includes a housing 110 that comprises a base plate 112, a plurality of sidewalls 114, and a top plate 120. The top plate 120 is the plate that is impacted by the hammering elements of the PIM distortion test apparatus 100, and hence will be referred to as a strike plate 120 herein. A plastic pad 122 is attached to the top surface of the strike plate 120. The plastic pad 122 may be very thin, and may be made of a relatively rigid plastic material so that the plastic pad 122 will not absorb a significant amount of force. The plastic pad 122 may protect both the top surface of the strike plate 120 and the lower surfaces of the devices under test 50 from damage. The plastic pad 122 may have an adhesive bottom surface and may be adhesively secured to the top surface of the strike plate 120 in some embodiments.

A plurality of internally threaded cylinders 116 are mounted around the periphery of the base plate 112 and extend upwardly therefrom. The strike plate 120 includes a plurality of apertures that are vertically aligned with the respective threaded cylinders 116 so that screws may be used to secure the strike plate 120 to the base plate 112. Additional screws are inserted through holes in the sidewalls 114 to secure the sidewalls 114 to the base plate 112 and to other of the sidewalls 114. The outer edge of the strike plate 120 may rest on the top surfaces of the sidewalls 114. Footers 118 (only one of which is visible in FIG. 4) which each comprise a leg with a base pad attached to a lower end thereof may be attached to and extend downwardly from the base plate 112. The footers 118 may be adjustable in some embodiments (e.g., the footers 118 may be received within threaded holes in the base plate 112 so that the length the each footer 118 extends below the base plate 112 may be adjusted).

Referring to FIGS. 3-6, a plurality of hammering elements 130 are mounted on the base plate 112. As shown best in FIG. 5, in the depicted embodiment, each hammering element 130 comprises a pneumatic actuator 130 that has a central cylinder 132 and a piston 134 that is moveably disposed within the cylinder 132. A head 136 may be attached to the top end of the piston 134. A compressed air port 138 is located adjacent the bottom of the cylinder 132. Four screws 139 are provided that are used to mount the pneumatic actuator 130 to the base plate 112. While not visible in the drawings, a spring is disposed in the bottom of each cylinder 132 that is attached to the bottom of each piston 134. These springs return the piston 134 to their respective resting positions, as will be explained below.

As shown in FIG. 6, the pneumatic actuators 130 may be located in various positions within the housing 110. In the depicted embodiment, four "central" pneumatic actuators 130 (labelled 1-4 in FIG. 6) extend upwardly in a square arrangement from the center of the base plate 112. The remaining four "outer" pneumatic actuators 130 (labelled 5-8 in FIG. 6) extend upwardly in a square arrangement from the outer regions of the base plate 112. When the device under test 50 has a small physical footprint, it may be placed on the middle of the strike plate 120 and a strike pattern that only activates the four central pneumatic actuators 130 may be used. When the device under test 50 has a larger footprint, a strike pattern that activates all eight pneumatic actuators may be used.

The pneumatic actuators 130 in the depicted embodiment are driven by air pressure that is supplied from an external compressed air source (not shown). The back sidewall 114 of housing 110 includes an opening 140. A grommet 142 may be mounted in the opening 140 that receives a conduit 144. A plurality of compressed air supply lines 146 are disposed within the conduit 144. The conduit 144 and the grommet 142 protect the compressed air supply lines 146 from damage. The compressed air supply lines 146 deliver compressed air from the compressed air source to the respective pneumatic actuators 130. A connector 148 is attached to the end of each compressed air supply line 146. The connectors 148 are received within the respective compressed air ports 138 of the cylinders 132. When the compressed air is delivered to one of the pneumatic actuators 130, the compressed air drives the piston 134 upwardly within the cylinder 132 into its activated position. When the supply of compressed air is cut off, the spring in the cylinder pulls the piston 132 back into its non-activated or "resting" position. The pneumatic actuators 130 are located directly underneath the strike plate 120 at a distance such that when the pistons 134 are activated the heads 136 of the pistons 134 impact the lower surface of the strike plate 120. A pneumatic electro-control valve 190 is disposed along each compressed air supply line 146, as will be explained in further detail below. These control valves 190 are used to control whether or not compressed air is delivered to each pneumatic actuator 130. In particular, by closing one of the pneumatic electro-control valves 190, compressed air is delivered through the compressed air supply line 146 to a respective one of the pneumatic actuators 130, causing the piston 134 of the pneumatic actuator 130 to fire and strike the lower surface of the strike plate 120.

The front sidewall 114 of the housing 110 includes an opening 115. A cap 117 may be used to cover the opening 115. In cases when a device under test 50 is very large, it may be beneficial to arrange two of the test stations 102 side-by-side, and an additional eight compressed air supply lines 146 (i.e., a total of sixteen compressed air supply lines 146) may be routed into the interior of the housing 110 through the conduit 144. Eight of the compressed air supply lines 146 may be used to supply compressed air to the eight respective pneumatic actuators 130 of the first test station, and the other eight compressed air supply lines 146 may be passed through the opening 115 (the cap 117 is removed) and used to supply compressed air to the eight respective pneumatic actuators 130 of the second test station 102.

As can further be seen in FIGS. 3 and 4, a retaining member 150 is mounted above the strike plate 120. In the depicted embodiment, the retaining member 150 comprises a pair of long screws 152 that are received within two of the threaded cylinders 116. The screws 152 are mounted on opposite sides of the strike plate 120. Each screw 152 may have a knob 154 attached to a head portion thereof to facilitate turning the screw 152 by hand. Each screw 152 passes through a respective opening 158 on a rod 156 that extends between the two screws 152. The rod 156 is positioned above the strike plate 120 and held in place by the screws 152.

Referring now to FIG. 7, a perspective view of the test station 102 of FIGS. 3-4 is illustrated with a device under test 50 mounted on the strike plate 120. As shown in FIG. 6, the device under test 50 is mounted on the upper surface of the strike plate 120 and the knobs 154 on the screws 152 are tightened so that the knobs 154 engage the rod 156 so that the rod 156 firmly presses against the upper surface of the device under test 50 to firmly hold the device under test 50 against the strike plate 120.

Figure 8:
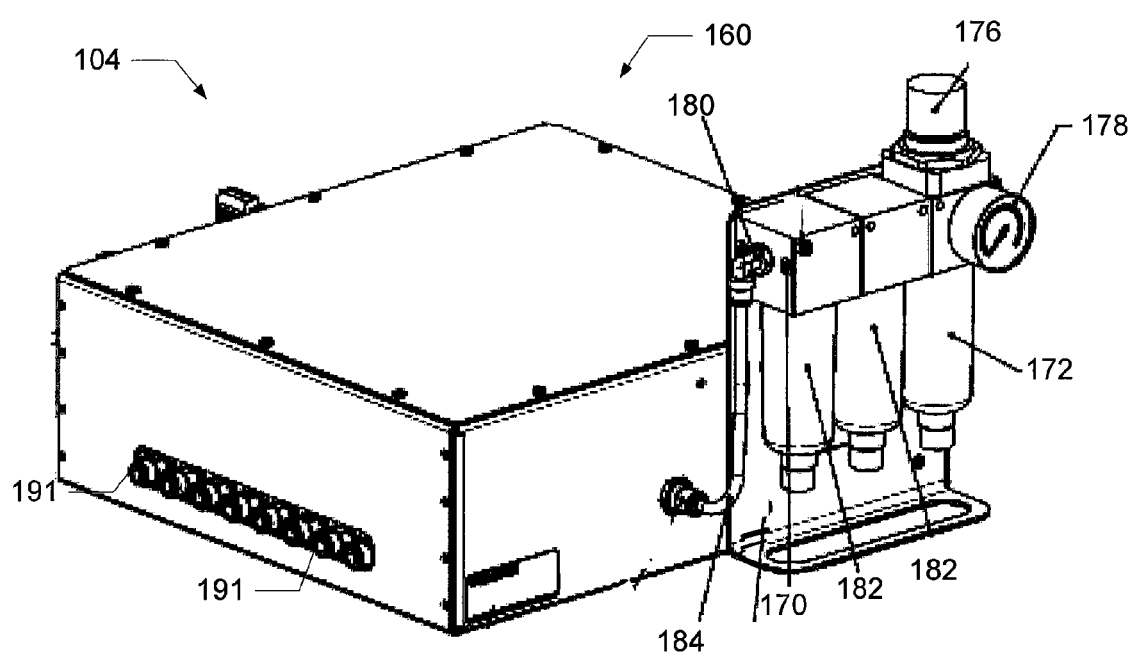
FIG. 8 is a perspective view of a control station of the PIM distortion test apparatus of FIG. 2.
Figure 9:
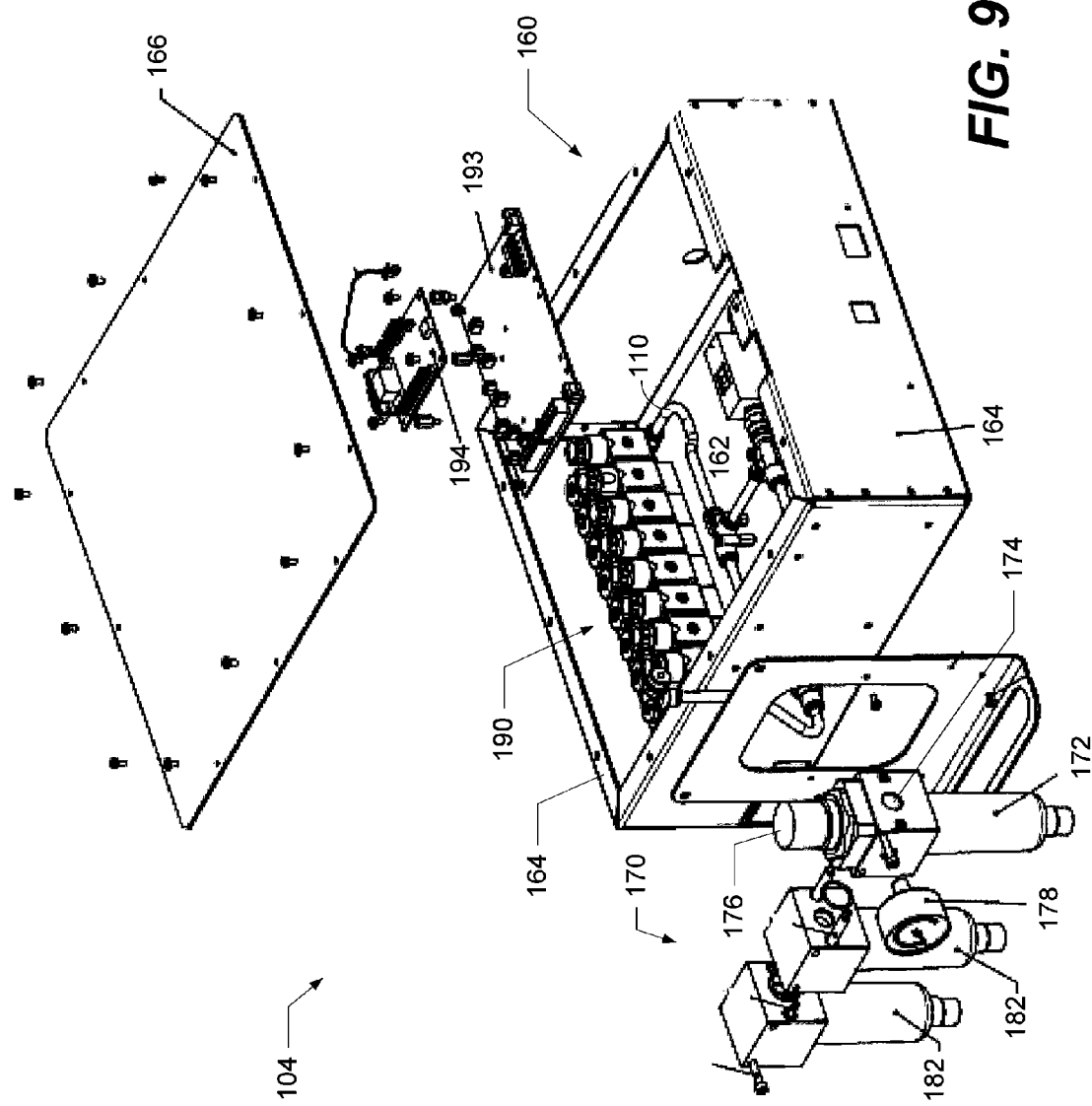
FIG. 9 is an exploded perspective view of the control station of FIG. 8.
Figure 10:
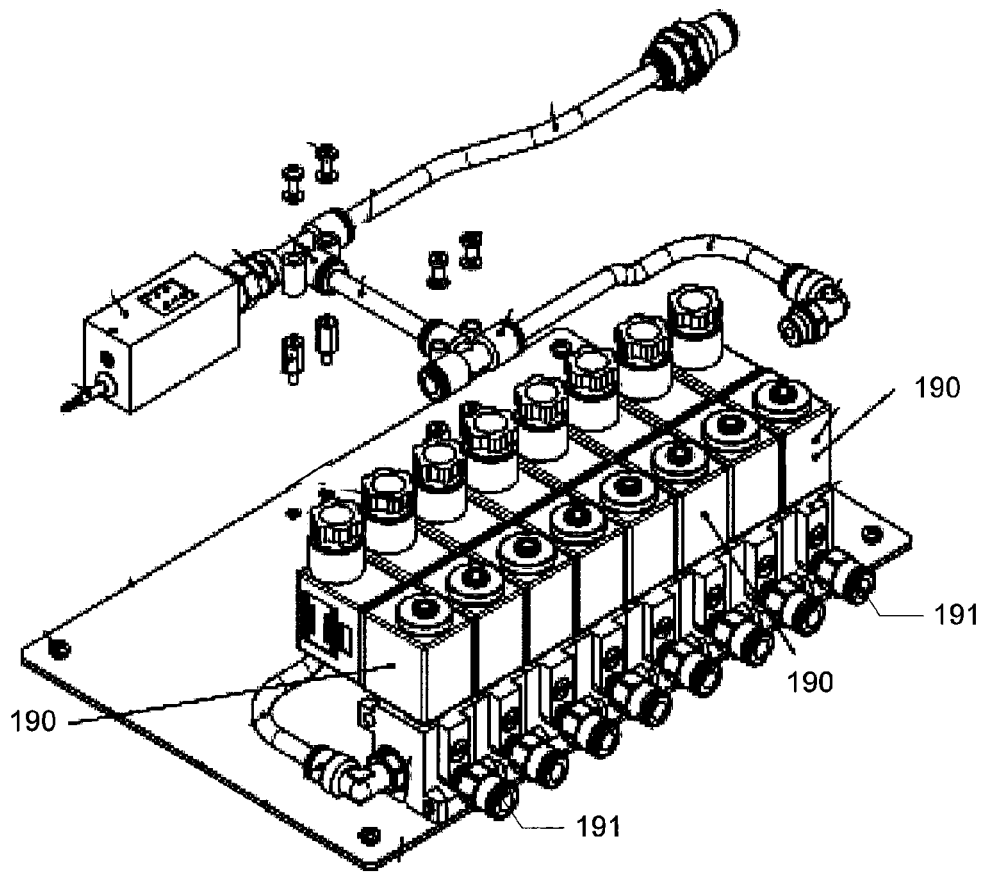
FIG. 10 is a perspective view of the air supply line and the pneumatic electro-control valves included in the control station of FIGS. 8-9.
Figure 11:
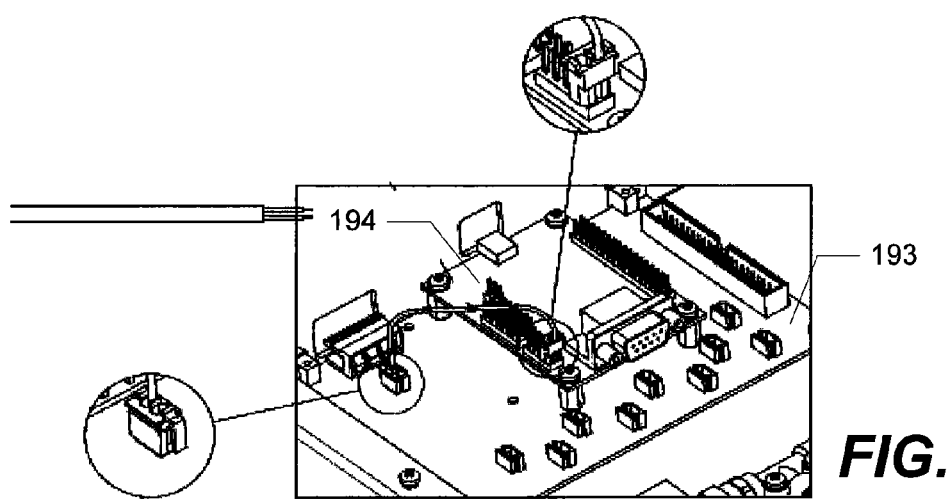
FIG. 11 is a perspective view of the printed circuit boards and associated circuitry included in the control station of FIGS. 8-9.

As noted above, the PIM test apparatus 100 includes the test station 102 and a control station 104. FIG. 8 is a perspective view of the a control station 104, and FIG. 9 is an exploded perspective view of the control station 104. FIG. 10 is a perspective view of the air supply line and the pneumatic electro-control valves 190 included in the control station 104, and FIG. 11 is a perspective view of the printed circuit boards and associated circuitry included in the control station 104.

Referring first to FIGS. 8-9, it can be seen that the control station 104 includes a housing 160 that comprises a base plate 162, a plurality of sidewalls 164, and a top plate 166 that are held together by a plurality of screws. A pressure regulator unit 170 is mounted on the exterior of the housing 160. The pressure regulator unit 170 includes a pressure regulator 172 that has an input port 174 that receives a supply line (not shown) from a separate compressed air source (not shown). The pressure regulator unit 170 further includes an adjustment knob 176, a pressure gauge 178 and an output port 180. The pressure gauge 178 indicates the pressure of the compressed air at the output port 180. The adjustment knob 176 may be used to adjust the pressure of the compressed air at the output port 180. In the embodiment of FIGS. 2-11, the pressure regulator unit 160 delivers compressed air having the same pressure to all eight pneumatic electro-control valves 190, and hence all eight pneumatic actuators 130 may be designed to impact the strike plate 120 with the same force blows. In other embodiments, it would be possible to individually adjust the force delivered by each pneumatic actuator 130. The pressure regulator unit 170 further includes a pair of filters 182 that may remove humidity from the compressed air. A supply line 184 is attached to the output port 180. The supply line 184 feeds the compressed air into the interior of the housing 160.

As shown in FIG. 9, the above-referenced pneumatic electro-control valves 190 are mounted along the back sidewall 164 of the housing 160. In the depicted embodiment, a total of eight pneumatic electro-control valves 190 are provided, namely one for each pneumatic actuator 130. Additional air supply piping 192 is used to feed compressed air to the pneumatic electro-control valves 190 from the supply line 184 that terminates into the sidewall 164 of housing 160. As shown in FIGS. 9 and 11, electronic circuitry is mounted on a pair of printed circuit boards 193,

194. Printed circuit board 193 provides a wired (USB) interface to an external control computer (not shown). Printed circuit board 194 includes circuitry that individually controls the eight pneumatic electro-control valves 190. Each of the pneumatic electro-control valves 190 is electrically connected to the printed circuit board 194 via individual electrical connections (not shown). Each pneumatic electro-control valve 190 has an output port 191. While not shown in the figures, it will be appreciated that the compressed air supply lines 146 terminate into the respective output ports 191 to provides a route for delivering compressed air to each pneumatic actuator 130.

Each pneumatic electro-control valve 190 is individually controlled via the external control computer (or some other processor). In particular, under control of the external computer, each pneumatic electro-control valve 190 may be opened to allow compressed air to feed through the associated compressed air supply line 146 to a corresponding pneumatic actuator 130, or may be closed so that compressed air is not fed to the corresponding pneumatic actuator 130. As discussed above, feeding compressed air to a pneumatic actuator 130 causes the pneumatic actuator 130 to "fire" whereby the piston 134 thereof is driven upwardly to impact the strike plate 120. When the supply of compressed air is stopped to the pneumatic actuator 130, the piston 134 returns to its "rest" position within the cylinder 132. The pneumatic electro-control valves 190 may be used to individually "fire" the pneumatic actuators 130 according to a strike pattern that specifies the sequence in which the pneumatic actuators 130 are fired (and note that the pneumatic actuators 130 may be fired one at a time and/or in groups) and the timing between successive firings, all under the control of, for example, a program running on the external computer. While in the depicted embodiment a USB interface is used to allow the external controller to control the pneumatic electro-control valves 190, it will be appreciated that in other embodiments the pneumatic electro-control valves 190 may be controlled via a different wired interface, via a wireless interface such as a Bluetooth connection, or via a controller that is part of the PIM distortion test apparatus 100.

As discussed above with reference to FIG. 1, the PIM distortion testing apparatus according to embodiments of the present invention such as PIM distortion test apparatus 100 may be used to measure the PIM distortion performance of various products including, for example, RF amplifiers, duplexers, cross-band couplers, interference mitigation filters, multiplexers and the like. These test apparatus may also be used to measure PIM distortion in antennas and even in coaxial cable junctions, if desired. As discussed above, the PIM test is conducted by generating RF signals (e.g., using a signal generator), amplifying the RF signals to an appropriate power level, running these amplified signals through a device under test, filtering the signals output from the device under test to remove signals that are at frequencies that are outside a frequency range of interest (e.g., the receive frequency band), and then recording the signal power in the frequency range of interest as a function of time. Typically, the PIM specification for a device under test will require that the total received signal power in the frequency band of interest stay beneath a certain level (which may be relative to the level of the signals input into the device under test) during the duration of the PIM distortion test. It will be appreciated, however, that other protocols may be used to determine whether or not a particular device under test exhibits acceptable or "passing" PIM distortion performance.

It should also be noted that while not shown in FIG. 1, a PIM distortion test may also measure PIM distortion at the input port to the device under test which reflects reflected PIM distortion.

As discussed above, the PIM distortion test may include both a static test portion where the hammering elements are not fired and a dynamic portion where the hammering elements are fired. PIM distortion performance may be better or worse during either segment. For example, in the case of a "dirty" device under test that has metal shavings in the interior, the hammering may act to dislodge such metal shavings from surfaces that tend to generate PIM distortion or, instead, may move such metal shavings to such surfaces. Thus, the use of both static and dynamic PIM distortion testing may provide more accurate results.

The inclusion of the strike plate 120 may simplify the set-up required for a dynamic PIM distortion test since it may make the PIM distortion test apparatus somewhat independent of the shape of the device under test. As noted above, a wide variety of different devices such as coaxial connector junctions, filters, couplers, amplifiers, duplexers and other RF components and antennas may be subjected to dynamic PIM distortion testing, and these devices may have greatly varied shapes. As the test apparatus 100 allows the device under test to simply be mounted so that the device under test contacts the strike plate 120, the test apparatus may accommodate a wide variety of devices under test and still provide a mechanism for applying repeated contact forces to the device under test in a fully repeatable manner.

An alternative approach to using a strike plate is to use hammering elements that are moveable so that the hammering elements can be moved to directly strike various portions of a device under test. Such an approach, however, may greatly increase the complexity and cost of the test apparatus. PIM distortion test apparatus that are designed according to such an approach may only work with a limited numbers of different devices under test, and specifically designed fixtures may be required in order to meet each the shape of each different product under test. It also may take longer to perform the set-up for each PIM distortion test performed using such test apparatus. By designing the device to include a strike plate that is between the hammering elements and the device under test the present inventors were able to simplify both the test apparatus and the test set-up while providing a test apparatus that is suitable for performing dynamic PIM distortion testing on a wide variety of devices.

It will be appreciated that the PIM distortion test apparatus 10 and 100 that are discussed above are example embodiments, and that many changes could be made to these devices without departing from the scope of the present invention. For example, while the test apparatus uses pneumatic actuators 130 as the hammering elements, other hammering elements could be used. For instance, in another embodiment, the pneumatic actuators 130 could be replaced with electrically powered actuators. In another embodiments rotating wheels with a cammed surface could be used. A variety of other hammering elements could also be used.

As another example, the strike plate 120 is implemented as a thin metal plate in the test apparatus 100. It will be appreciated, however, that thicker plates may be used and/or plates made of other materials that are sufficiently rigid and/or which do not absorb too much energy. The strike plate also need not be a planar plate.

As yet another example, a wide variety of retaining members may be used to hold the device under test on the test apparatus. For example, adjustable side plates could be provided above the strike plate that may be used to press against the sides of the device under test to hold the device under test firmly on the strike plate 120. In other embodiments, mechanical clamps may be provided that hold the device under test in place. It will be appreciated that a wide variety of retention elements could be used. In fact, with respect to devices under test that are quite heavy it has been found that the dynamic PIM test results do not vary significantly regardless of whether or not the retaining member is used, as the weight of the device under test may be sufficient to firmly hold the device under test on the strike plate.

In some embodiments, the processor may control all aspects of the PIM distortion test. For example, the processor may control the signal generator to generate and transmit the appropriate RF test signals, may control the spectrum analyzer to receive the PIM test results and may control pneumatic control valves (or other elements) that control the hammering elements.

Figure 12:
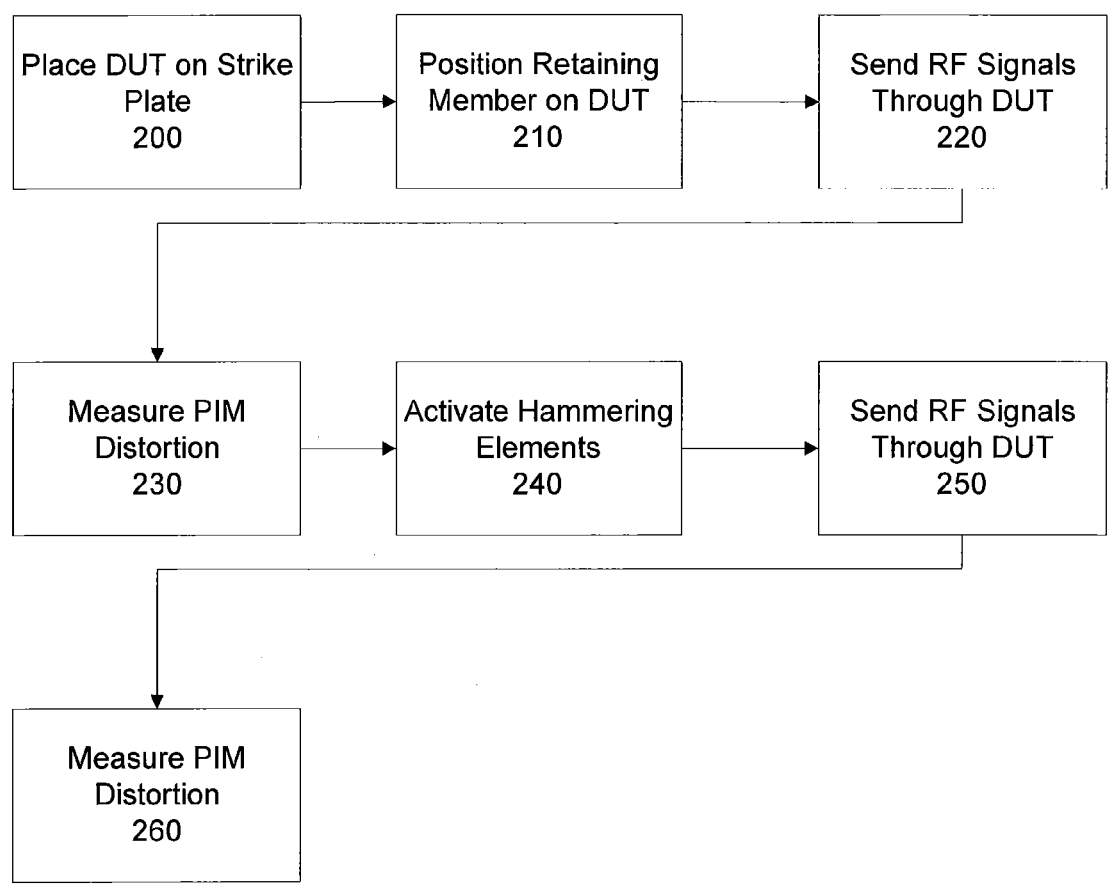
FIG. 12 is a flow chart illustrating a method of performing PIM distortion testing according to embodiments of the present invention.

FIG. 12 is a flow chart illustrating a method of performing PIM distortion testing according to embodiments of the present invention. As shown in FIG. 12, operations may begin with a device under test ("DUT") being placed on an upper surface of a strike plate of a testing station that includes a plurality of hammering elements located underneath the strike plate (block 200). Next, a retaining member may be positioned to engage at least one of a top surface or a side surface of the device under test to pin the device under test against the strike plate (block 210). At least two RF signals may then be transmitted through the device under test to perform a static PIM distortion test (block 220). A spectrum analyzer may be used to measure PIM distortion generated in the device under test (block 230). The testing station may then be operated so that the hammering elements are activated according to a pre-programmed sequence, where activation of each hammering element causes a moveable striking member of the hammering element to extend upwardly to impact a lower surface of the strike plate (block 240). The RF signals may be transmitted through the device under test while the hammering elements are activated (block 250). The spectrum analyzer may again be used to measure PIM distortion generated in the device under test while the hammering elements are activated (block 260).

While the present invention has been described above primarily with reference to the accompanying drawings, it will be appreciated that the invention is not limited to the illustrated embodiments; rather, these embodiments are intended to fully and completely disclose the invention to those skilled in this art. In the drawings, like numbers refer to like elements throughout. Thicknesses and dimensions of some components may be exaggerated for clarity.

Spatially relative terms, such as "under", "below", "lower", "over", "upper", "top", "bottom" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity. As used herein the expression "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including" when used in this specification, specify the presence of stated features, operations, elements, and/or components, but do not preclude the presence or addition of one or more other features, operations, elements, components, and/or groups thereof.

Herein, the terms "attached", "connected", "interconnected", "contacting", "mounted" and the like can mean either direct or indirect attachment or contact between elements, unless stated otherwise.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A passive intermodulation ("PIM") distortion test apparatus, comprising:
    a housing;
    a plurality of hammering elements disposed within the housing, each hammering element including a moveable striking member that is configured to move between a resting position and an activated position;
    a strike plate positioned above the hammering elements, wherein a bottom surface of the strike plate is positioned at a distance above the hammering elements such that the moveable striking members of the hammering elements impact the strike plate when moved into their activated positions; and
    a retaining member that is configured to hold a device under test on a top surface of the strike plate while a PIM distortion test is performed on the device under test.

2. The PIM distortion test apparatus of claim 1, wherein the hammering elements comprise pneumatic actuators.

3. The PIM distortion test apparatus of claim 2, further comprising at least one pneumatic electro-control valve that is configured to control operation of at least one of the pneumatic actuators.

4. The PIM distortion test apparatus of claim 3, wherein the at least one pneumatic electro-control valve is controlled by an external processing device via a wired or wireless interface.

5. The PIM distortion test apparatus of claim 2, wherein operation of the pneumatic actuators are controlled according to a software program.

6. The PIM distortion test apparatus of claim 2, further comprising a pressure regulator that may be used to control a strike force of at least one of the pneumatic actuators.

7. The PIM distortion test apparatus of claim 2, wherein the retaining member comprises a support member having an adjustable height that is configured to contact an upper surface of the device under test.

8. The PIM distortion test apparatus of claim 2, wherein the strike plate comprises a metal strike plate.

9. The PIM distortion test apparatus of claim 2, further comprising a thin plastic sheet on the upper surface of the strike plate.

10. The PIM distortion test apparatus of claim 2, in combination with signal generating equipment that transmits at least two radio frequency signals to the device under test and signal analysis equipment that measures PIM distortion generated in the device under test.

11. The PIM distortion test apparatus of claim 10, further comprising a controller that includes a processor that controls operation of the hammering elements, the signal generation equipment and the signal analysis equipment.

12. The PIM distortion test apparatus of claim 11, wherein the controller comprises a control station that includes at least one pneumatic electro-control valve that is configured to control operation of at least one of the pneumatic actuators and an external computer running a software program that controls the control station, the signal generating equipment and the signal analysis equipment.

13. A method of performing a passive intermodulation ("PIM") distortion test, the method comprising:
placing a device under test on an upper surface of a strike plate of a test station that includes a plurality of hammering elements located underneath the strike plate;
positioning a retaining member to engage at least one of a top surface or a side surface of the device under test to pin the device under test against the strike plate;
activating the hammering elements of the test station according to a pre-programmed sequence, wherein activation of each hammering element causes a moveable striking member of the hammering element to extend upwardly to impact a lower surface of the strike plate;
transmitting at least two RF signals through the device under test while the hammering elements are activated according to the pre-programmed sequence; and
using a spectrum analyzer to measure PIM distortion generated in the device under test while the hammering elements are activated.

14. The method of claim 13, wherein each hammering element comprises a pneumatic actuator.

15. The method of claim 13, further comprising using the spectrum analyzer to measure PIM distortion generated in the device under test during a time period before the hammering elements are activated.

16. The method of claim 13, further comprising controlling an RF signal generator that generates the at least two RF signals and controlling the spectrum analyzer using a software program running on an external computer, the software program also controlling the hammering elements to activate in the pre-programmed sequence.

17. The method of claim 13, further comprising setting a pressure regulator to control the force with which the hammering elements impact the strike plate.

18. The method of claim 13, wherein the retainer comprises a support member having an adjustable height that is configured to contact an upper surface of the device under test.

19. The method of claim 13, wherein the strike plate comprises a metal strike plate.

20. The method of claim 13, wherein activating the hammering elements of the test station comprises only activating an inner subset of the hammering elements.

* * * * *